United States Patent [19]

Harman et al.

[11] Patent Number: 5,752,517
[45] Date of Patent: May 19, 1998

[54] INTRAOPERATIVE ULTRASOUND PROBES FOR ULTRASONIC EXAMINATION DURING SURGERY

[75] Inventors: Larry L. Harman, Boalsburg; Brian K. Moist, McVeytown; Gyke McCardle, Burnham, all of Pa.; Kip R. Nelson, Mill Creek, Wash.; Timothy F. Nordgren, Bothell, Wash.; Joseph Lindsay Ungari, Everett, Wash.; David M. Becker, Lewistown, Pa.

[73] Assignee: Advanced Technology Laboratories, Inc., Bothell, Wash.

[21] Appl. No.: 731,409

[22] Filed: Oct. 18, 1996

[51] Int. Cl.⁶ .................................................. A61B 8/00
[52] U.S. Cl. .................................................. 128/662.03
[58] Field of Search ................... 128/660.07, 660.08, 128/660.09, 660.1, 662.03, 661.01

[56] References Cited

U.S. PATENT DOCUMENTS

| | | | |
|---|---|---|---|
| 4,535,781 | 8/1985 | Hetz | 128/660 |
| 4,898,177 | 2/1990 | Takano et al. | 128/662.03 |
| 4,972,839 | 11/1990 | Angelsen | 128/660.1 |
| 5,088,500 | 2/1992 | Wedel | 128/662.06 |
| 5,152,293 | 10/1992 | Vonesh et al. | 128/662.03 |
| 5,482,047 | 1/1996 | Nordgren et al. | 128/662.03 |

OTHER PUBLICATIONS

"A Complete Family of High Density Probes" Hitachi Medical Corp.

*Primary Examiner*—George Manuel
*Attorney, Agent, or Firm*—W. Brinton Yorks, Jr.

[57] ABSTRACT

Intraoperative ultrasound probes are described having contoured side surfaces which enable the probe to be held between the fingers of a surgeon during a surgical ultrasound procedure. The probes advantageously permit the surgeon to conduct a tactile examination of organs of a patient with the hand and fingertips while holding the probe.

19 Claims, 6 Drawing Sheets

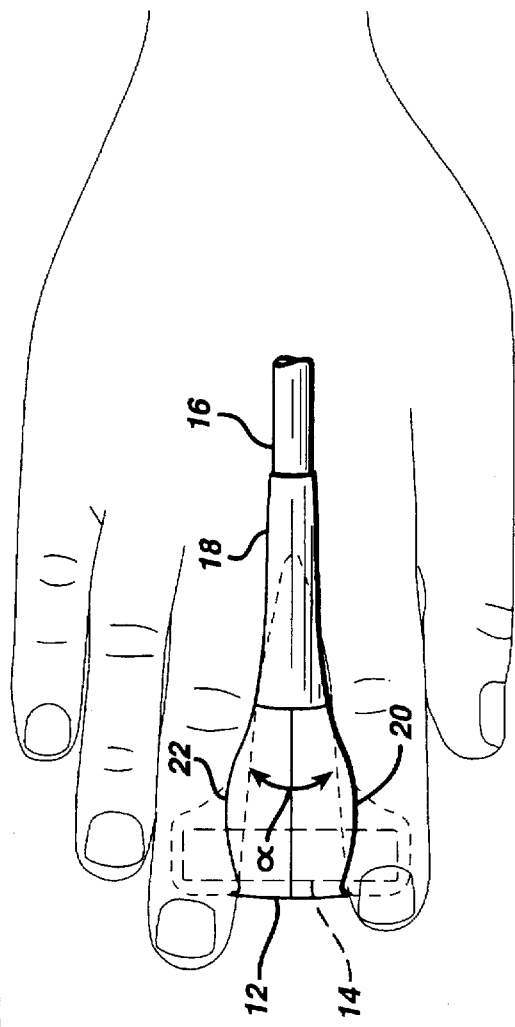
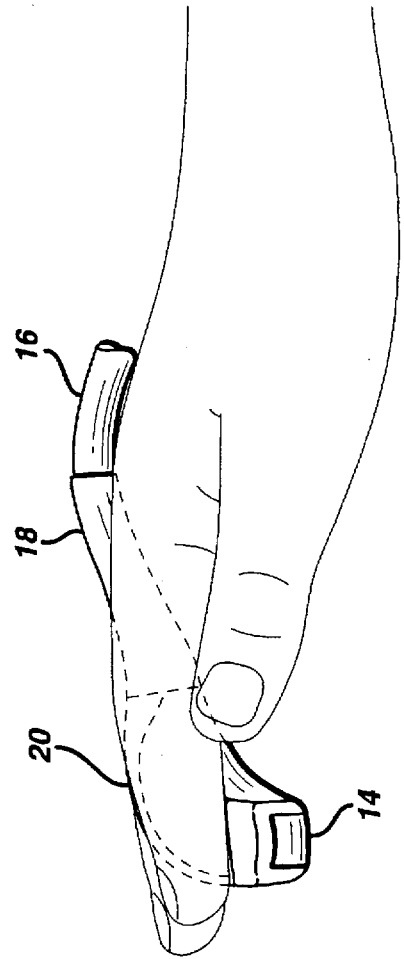
FIG. 3a
FIG. 3b

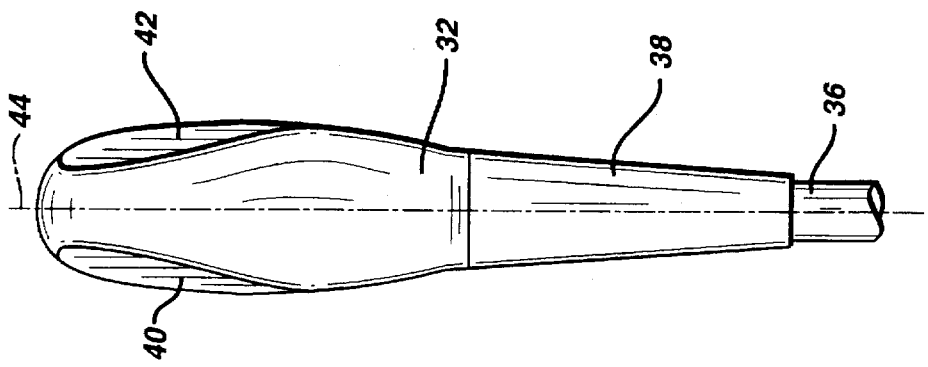
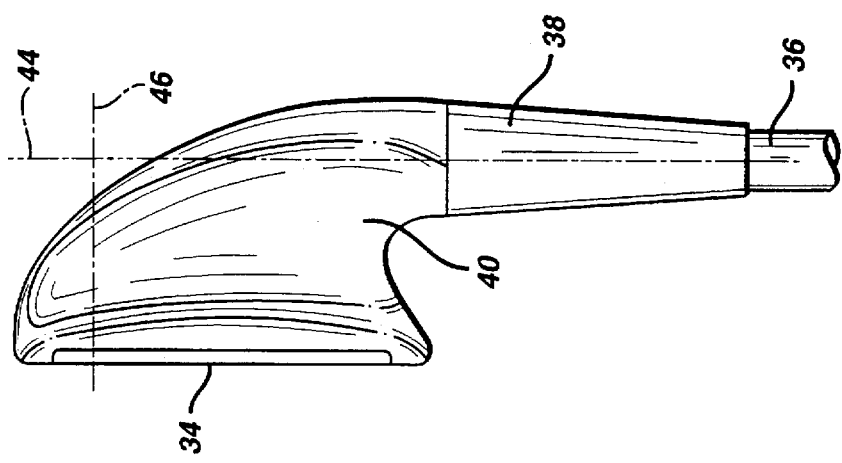
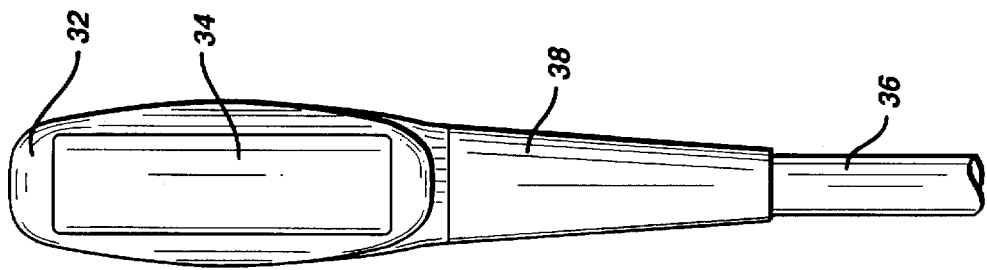

INTRAOPERATIVE ULTRASOUND PROBES FOR ULTRASONIC EXAMINATION DURING SURGERY

This invention relates to ultrasonic diagnostic probes or scanheads and, in particular, to ultrasound probes which are uniquely suited for imaging and diagnosing organs and vessels of the body during surgery.

Ultrasonic diagnostic imaging probes, which generally find application during noninvasive procedures, can also be used during surgical procedures. One such procedure where ultrasonic imaging probes have particular utility is during vascular surgery. During vascular surgery, ultrasonic imaging probes can be utilized to image and diagnose the interior of carotid arteries. Another procedure where ultrasonic imaging probes have utility is during transplant surgery where, for example, the ultrasonic imaging probe can be used to verify successful attachment and function of renal arteries. Another use is pancreatic or liver surgery, where ultrasound may be used to detect any abnormalities resident in these organs.

Surgical ultrasound probes are preferably small and as easy to manipulate as surgical instruments. When surgical probes are used during abdominal surgery, the surgeon is first concerned with locating the lesion or region of an organ that is the subject of the diagnosis. A conventional technique employed by a surgeon to locate masses or other pathology is through palpation, where the surgeon is feeling an organ with the finger tips to locate the pathology. A surgical ultrasound probe should preferably be small, comfortable, and easy for the surgeon to use, and should also enable the surgeon to examine an organ through palpation while conducting the ultrasonic examination.

In accordance with the principles of the present invention an ultrasonic imaging probe is provided for surgical applications. The probe comprises an ultrasonic transducer and an enclosure contoured to be held between the fingers of the surgeon. The probe enables the surgeon to palpate an organ while holding the probe in a natural and comfortable manner. The probe cable can be draped over the surgeon's hand and out of the way of the surgical examination.

In the drawings:

FIGS. 3a and 3b illustrate the probe of FIG. 1 during surgical use;

FIGS. 5a–5c are bottom plan, top plan, and side views; and

Figure 1:
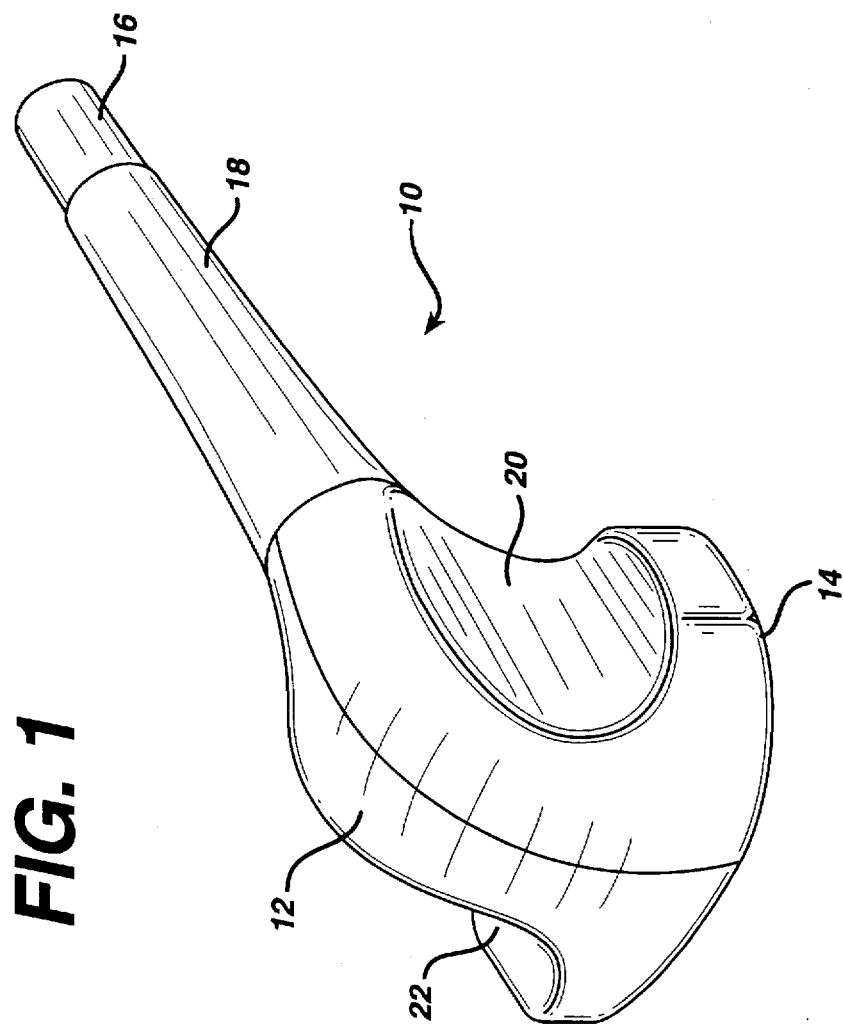
FIG. 1 is a perspective view of an intraoperative ultrasound probe constructed in accordance with the principles of the present invention.

Referring first to FIG. 1, an intraoperative ultrasound probe 10 constructed in accordance with the principles of the present invention is shown. In this embodiment the ultrasound probe 10 includes a curved array transducer housed inside an enclosure 12 and located behind a lens cover 14 through which ultrasonic energy is transmitted and received by the transducer. The lens cover insulates and protects the array transducer from the surgical environment. A cable 16 of a plurality of multifilament coaxial wires enters the enclosure 12 through a strain relief 18, and the coaxial wires are connected to individual piezoelectric elements of the array transducer by one or more termination assemblies as described in U.S. Pat. No. 5,482,047.

In accordance with the principles of the present invention, opposing sides 20 and 22 of the enclosure 12 are formed in a contoured shape. These concave sides enable the ultrasound probe to be conveniently held between the fingers of a surgeon during use as described below.

Figure 2B:
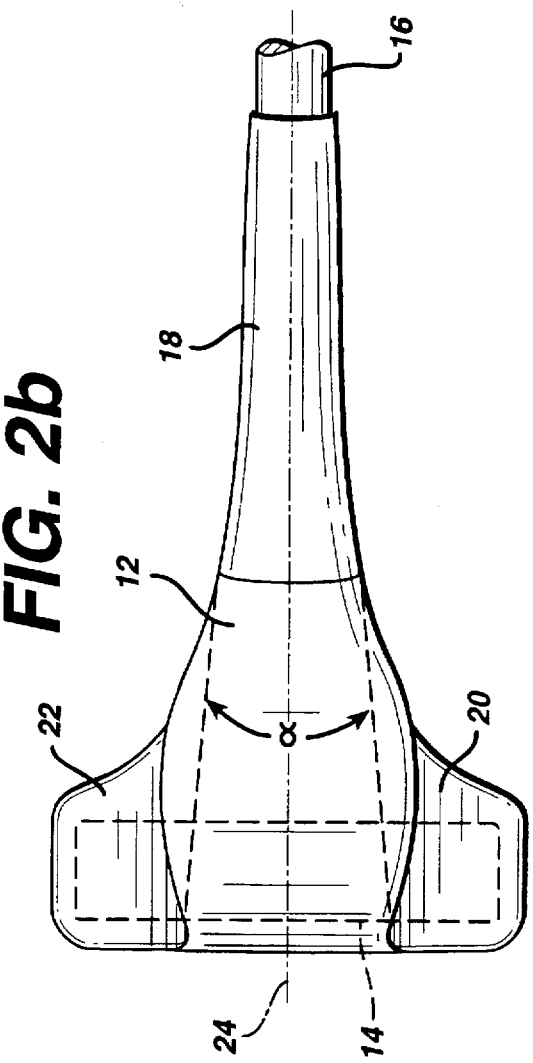
FIGS. 2a–2c are distal, plan, and side views of the probe of FIG. 1.
Figure 2C:
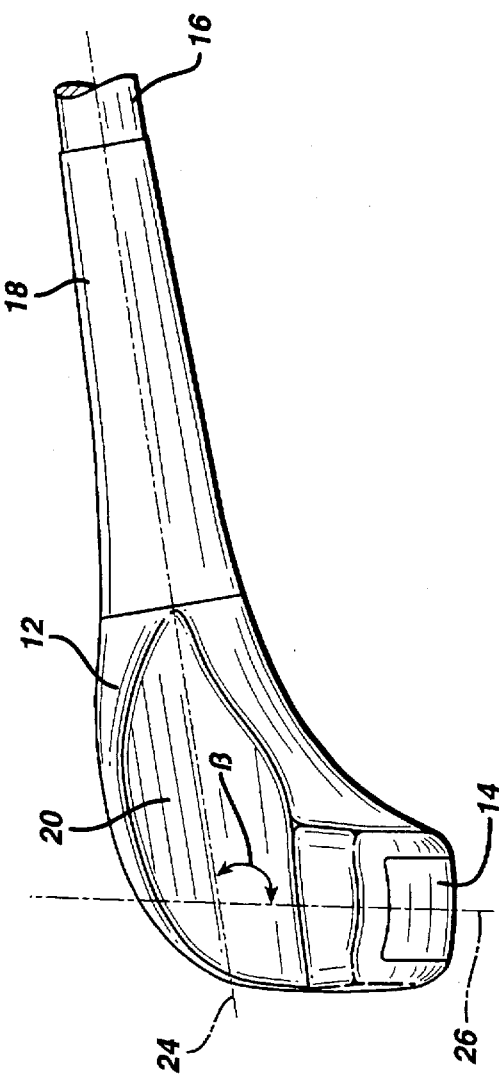
Figure 2A:
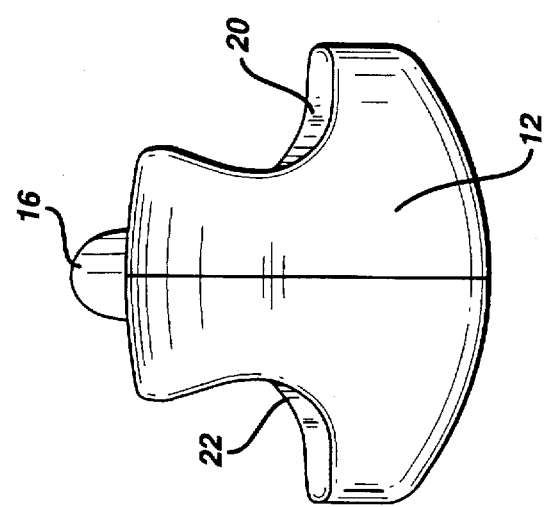

The ultrasound probe of FIG. 1 is shown in distal, plan, and side views in FIGS. 2a, 2b, and 2c, respectively. The distal end view of FIG. 2a clearly shows the contoured sides 20,22 of the enclosure 12. In the top plan view of FIG. 2b it is seen that in this embodiment the surfaces of the contoured sides are slightly tapered toward each other at an angle $\Delta$ from the distal end of the enclosure to the point of attachment of the strain relief 18. This slight tapering permits a more natural fit of the ultrasound probe between the surgeon's fingers as discussed below. The side view of FIG. 2c illustrates the intersecting angle $\beta$ of two centerlines, line 24 of the strain relief and cable and line 26 drawn normal to the surface of the lens cover 14. It is seen that the angle $\beta$ is an obtuse angle, causing the strain relief and cable to have an upward orientation when the transducer and lens cover are held against the surface of an organ or tissue.

Turning to FIGS. 3a and 3b, the ultrasound probe of FIG. 1 is shown while held between the ungloved fingers of a user. As these drawings illustrate, the enclosure 12 is grasped by engaging the contoured sides 20,22 between the fingers. Unlike intraoperative probes of the prior art which must be grasped by wrapping the fingers around the probe or between the thumb and fingers, an ultrasound probe of the present invention can be held comfortably between the fingers, freeing the thumb and palm surface of the hand and fingers for manipulation within the surgical opening and around organs in the body of the patient. In particular, it is seen that the fingertips are able to extend forward from the ultrasound probe. These features enable the surgeon to palpate an organ for suspected masses and lesions while holding the ultrasound probe at the same time. Significantly, the surgeon's sensitive fingertips are free to probe tissues and organs of the surgical site ahead of the ultrasound probe. The surgeon can simultaneously palpate an organ or tissue of the body while ultrasonically scanning the body at the same time.

When a person's fingers are closed next to each other, they are essentially in a parallel relationship. But as the fingers are spread, they naturally assume a general V-shape. The tapered angle $\alpha$ of the contoured side surfaces adapt the ultrasound probe to this natural V-shape, as seen in FIG. 3a. The angle $\beta$ between the strain relief 18 and cable 16, and a line normal to the surface of the lens cover 14 cause the cable to pass naturally over the top of the hand and away from the surgical site when the array is held normal to the surface of the organ with comfortably relaxed fingers, as seen in FIG. 3b. Thus, the cable 16 is directed away from the surgical site of the organ or tissue which is in contact with the lens cover 14 and the fingertips and palm surface of the surgeon's hand.

Additionally, if desired, the ultrasound probe may be extended beyond the surgeon's hand and deeper into the body by grasping the cable 16 or strain relief 18 at the back of the ultrasound probe and extending the ultrasound probe forward. This capability is useful when examining limited access areas of a surgical site, such as those located over the "dome" of the liver.

Figure 4:
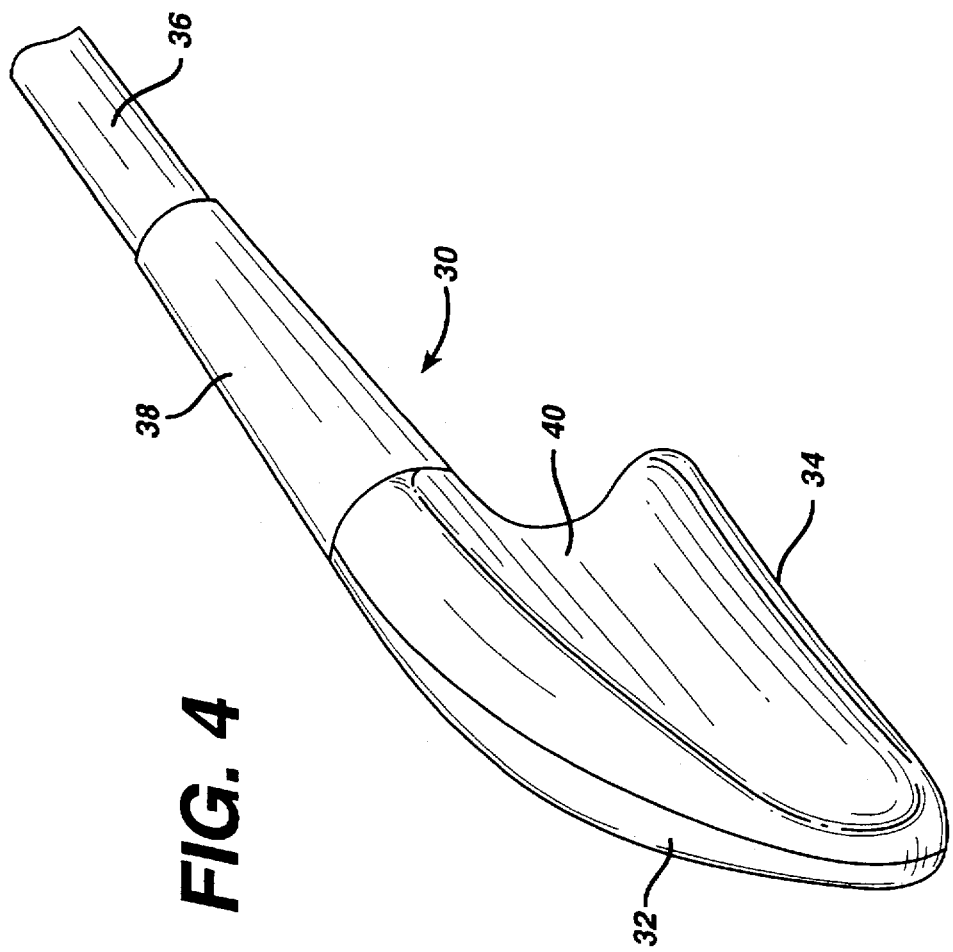
FIG. 4 is a perspective view of a second embodiment of the present invention.

Turning now to FIG. 4, a second embodiment 30 of an ultrasound probe of the present invention is shown. In contrast to the embodiment of FIG. 1, where the array transducer was oriented transverse to the axis of the cable, in the embodiment of FIG. 4 the array transducer is oriented in a parallel relationship to the cable axis. The array transducer of the second embodiment is a flat linear array, although a curved array transducer could also be employed. The array transducer is located in an enclosure 32 with contoured sides 40 and 42 (not seen in this view), and directs and receives ultrasonic energy through a lens cover 34. The probe enclosure is seen to exhibit a narrow distal nose, enabling the probe to be easily maneuvered around and between tightly spaced organs. A multifilament cable 36 with coaxial wires connected to the elements of the array transducer exits from the proximal end of the enclosure 32 through a strain relief 38.

FIGS. 5a, 5b, and 5c are bottom plan, side, and top plan views of the ultrasound probe of FIG. 4, respectively. In FIG. 5a the lens cover 34 which covers the array transducer is seen facing the viewer, and is seen to have its longitudinal axis in parallel with the cable 36. FIG. 5b shows a line 46 drawn normal to the surface of the lens cover 34 and intersecting the axis 44 of the cable 36 in an orthogonal orientations FIG. 5c is a top plan view of the second embodiment where the distal extensions of the contoured surfaces 40 and 42 on the opposite sides of the enclosure 32 can be seen. In this second embodiment these contoured surfaces are not oriented toward each other at an obtuse angle as were the contoured surfaces of the first embodiment, but are parallel to each other.

Figure 6A:
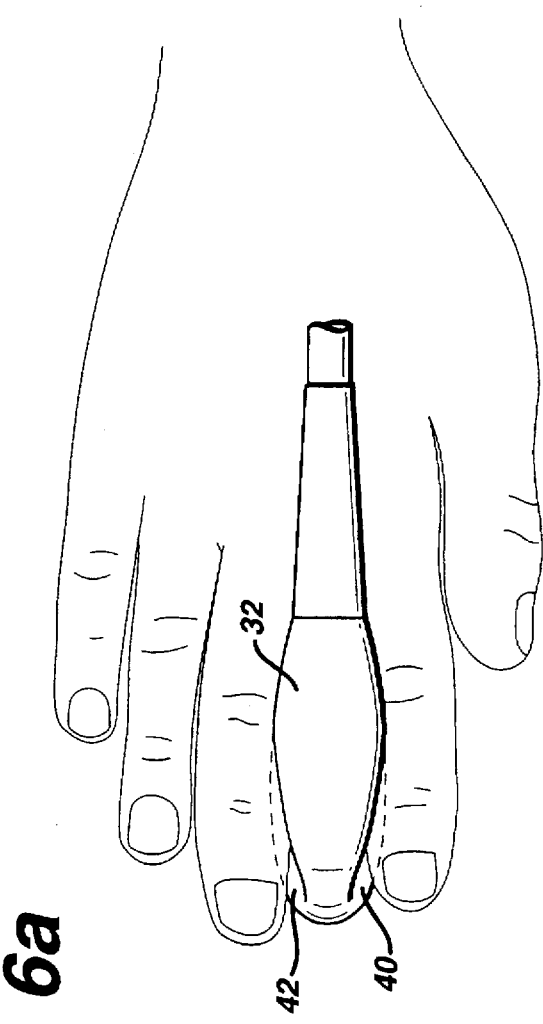
FIGS. 6a and 6b illustrate the probe of FIG. 4 during surgical use.
Figure 6B:
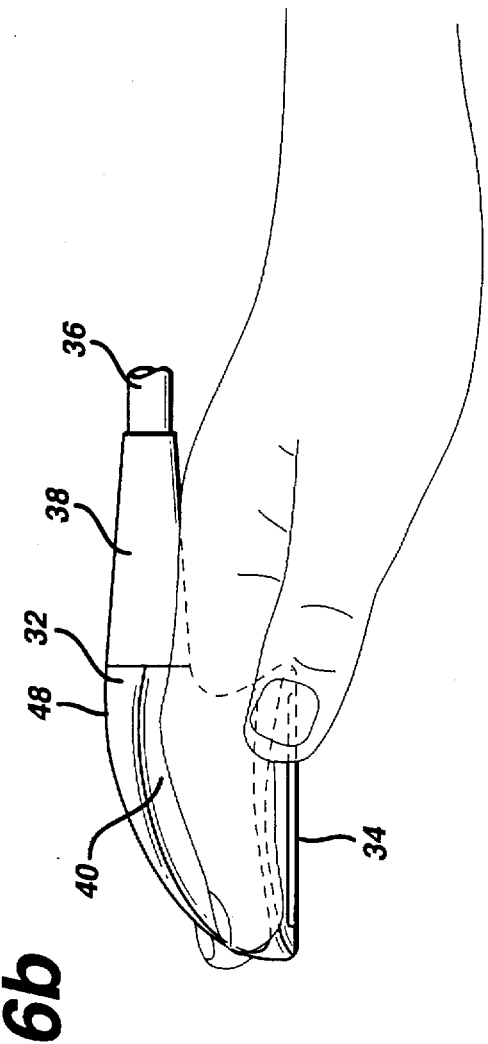

FIGS. 6a and 6b illustrate the ultrasound probe of FIG. 4 while held between the ungloved fingers of a user. As with the first embodiment, it is seen that the palm surface of the surgeons hand and fingers and fingertips are free to perform palpation while holding the ultrasound probe. The ultrasound probe fits comfortably between the fingers and the opposing fingers engage the contoured sides 40, 40 of the enclosure 32. Because the longitudinal axes of the array transducer and cable are parallel, the enclosure 32 is able to maintain a slender width profile. The narrow width of the ultrasound probe means that the fingers of the user are not spread apart very far while holding the ultrasound probe. Thus, the probe is held comfortably when the contoured side surfaces 40,42 are parallel to each other and not angled away from each other as in the previous embodiment.

FIG. 6b shows that the ultrasound probe of this embodiment has a high profile from the lens cover 34 to the opposite top surface 48, which enables the strain relief 38 and cable 36 to pass naturally over the top of the hand even when the lines 44,46 are orthogonal to each other and not at an obtuse angle.

What is claimed is:

1. An ultrasonic transducer probe which is especially useful for intraoperative examination comprising:

a linear or curvilinear ultrasonic transducer array;

means for coupling signals produced by said transducer array to an ultrasonic signal processor; and a unitary body housing said transducer array and having contoured sides which enable said probe to be held during use between two extended fingers of a user, with the tips of said extended fingers extending forward of the distal end of said body.

2. The ultrasonic transducer probe of claim 1, wherein said means for coupling comprises a cable.

3. The ultrasonic transducer probe of claim 2, wherein said cable comprises a multifilament cable connected to elements of said array transducer.

4. The ultrasonic transducer probe of claim 3, wherein said multifilaments comprise coaxial wires.

5. The ultrasonic transducer probe of claim 2, wherein said cable is attached to said body at a proximal end of said body so that said cable extends from said proximal end and rests on the back of the user's hand during use of the probe.

6. The ultrasonic transducer probe of claim 1, wherein said unitary body comprises a sealed, fluid-tight enclosure and wherein said contoured sides are on opposite sides of said enclosure.

7. The ultrasonic transducer probe of claim 5 wherein said means for coupling comprises a cable, and wherein said enclosure further encloses the connection of said cable to said transducer array.

8. The ultrasonic transducer probe of claim 5, wherein said contoured sides comprise external concave surfaces of said enclosure.

9. The ultrasonic transducer probe of claim 8, wherein said contoured sides are substantially parallel to each other.

10. The ultrasonic transducer probe of claim 1, wherein said means for coupling comprises a cable connected to said body and having a longitudinal axis which is oriented at an obtuse angle with respect to an axis extending normal to a surface of said probe through which ultrasonic energy is received.

11. The ultrasonic transducer probe of claim 1, wherein said means for coupling comprises a cable connected to said body and having a longitudinal axis which is oriented orthogonally with respect to an axis extending normal to a surface of said probe through which ultrasonic energy is received.

12. An ultrasonic transducer probe which is especially useful for intraoperative examination comprising:

a linear or curvilinear ultrasonic transducer array;

means for coupling signals produced by said transducer array to an ultrasonic signal processor; and a body housing said transducer array and having opposing concave contoured sides which enable said probe to be held during use between two extended fingers of a user, with the tips of said extended fingers extending forward of the distal end of said body, wherein said contoured sides are angled toward each other.

13. The ultrasonic transducer probe of claim 12, wherein said concave contoured sides have a distal end and a proximal end, and wherein said contoured sides are separated by a greater dimension at said distal end than at said proximal end.

14. The ultrasonic transducer probe of claim 13, wherein said means for coupling comprises a cable connected to said body at said proximal end.

15. The ultrasonic transducer probe of claim 14, wherein said cable comprises a multifilament cable connected to said ultrasonic transducer within said body.

16. An ultrasonic transducer probe which is especially useful for intraoperative examination comprising:

a linear or curvilinear ultrasonic array transducer for scanning an image plane and having a longitudinal dimension;

a cable having a longitudinal axis for coupling signals produced by said transducer to an ultrasonic signal processor; and a unitary enclosure housing said ultrasonic array transducer and connected to said cable such that said longitudinal dimension of said transducer array and the image plane of said transducer are oriented transverse to said longitudinal axis of said cable, said enclosure having contoured sides which enable said probe to be held during use between the fingers of a user.

17. The ultrasonic transducer probe of claim 16, wherein said cable is attached to said enclosure housing at a proximal end of said enclosure housing so that said cable extends from said proximal end and rests on the back of the user's hand during use of the probe.

18. An ultrasonic transducer probe which is especially useful for intraoperative examination comprising:
- a linear or curvilinear ultrasonic array transducer having a longitudinal dimension;
- a cable having a longitudinal axis for coupling signals produced by said transducer to an ultrasonic signal processor; and
- a unitary enclosure housing said ultrasonic array transducer and connected to said cable such that said longitudinal dimension of said transducer array and said longitudinal axis of said cable are oriented substantially parallel to each other, said enclosure having contoured sides which enable said probe to be held during use between two extended fingers of a user, with the tips of said extended fingers extending forward of the distal end of said body.

19. The ultrasonic transducer probe of claim 18, wherein said cable is attached to said enclosure housing at a proximal end of said enclosure housing so that said cable extends from said proximal end and rests on the back of the user's hand during use of the probe.

* * * * *